(12) United States Patent
Leong (10) Patent No.: US 12,201,280 B2
(45) Date of Patent: Jan. 21, 2025

(54) CONSOLE LIGHT GUIDE DEVICE

(71) Applicant: Alcon Inc., Fribourg (CH)

(72) Inventor: Kyle Leong, Tustin, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/637,629

(22) Filed: Apr. 17, 2024

(65) Prior Publication Data
US 2024/0358356 A1 Oct. 31, 2024

Related U.S. Application Data

(60) Provisional application No. 63/498,648, filed on Apr. 27, 2023.

(51) Int. Cl.
*A61B 17/00* (2006.01)
*A61B 90/00* (2016.01)
*F21V 8/00* (2006.01)

(52) U.S. Cl.
CPC .............. *A61B 17/00* (2013.01); *A61B 90/36* (2016.02); *G02B 6/002* (2013.01); *G02B 6/0068* (2013.01); *G02B 6/0073* (2013.01); *A61B 2017/00199* (2013.01)

(58) Field of Classification Search
CPC .............. A61B 17/00; A61B 90/36; A61B 2017/00199; G02B 6/002; G02B 6/0068; G02B 6/0073
See application file for complete search history.

(56) References Cited

U.S. PATENT DOCUMENTS

| | | | |
|---|---|---|---|
| 5,276,591 | A | 1/1994 | Hegarty |
| 7,246,932 | B2 | 7/2007 | Burtsev |
| 7,352,339 | B2 | 4/2008 | Morgan |
| 7,551,077 | B2 | 6/2009 | Raybuck et al. |
| 7,796,040 | B2 | 9/2010 | Mezhinsky |
| 7,934,862 | B2 | 5/2011 | Anandan |
| 7,956,341 | B2 | 6/2011 | Gao |
| 7,981,109 | B2 | 7/2011 | Avanzino |

(Continued)

FOREIGN PATENT DOCUMENTS

TW    I582353 B    5/2017

OTHER PUBLICATIONS

OSRAM, Application Note No. AN072 "Light guides" dated 2019 (11 pages).

(Continued)

*Primary Examiner* — Mary Ellen Bowman (57) ABSTRACT

A console light guide device for use with a control console includes an interconnected light tube array. The light tube array includes a translucent surface, a shaped body substantially surrounding an output connection port on an external face of a console panel, and linear branches arranged relative to the shaped body. Side-firing light-emitting diodes (LEDs) emit light into a corresponding end of the light tube array. An opaque light guard defines a shaped channel and branch channels. The light tube array nests within the opaque light guard such that light from the side-firing LEDs is emitted uniformly through the translucent surface without any internal scattering or bleeding of the light within the console. A control console such as an ophthalmic surgical console is also disclosed herein that includes the console light guide device.

19 Claims, 5 Drawing Sheets

(56) References Cited

U.S. PATENT DOCUMENTS

| | | |
|---|---|---|
| 8,109,644 B2 | 2/2012 | Bierhuizen |
| 9,343,003 B2 | 5/2016 | Podd |
| 9,498,300 B1 | 11/2016 | Sanchez, Jr. |
| 9,823,404 B2 | 11/2017 | Ouderkirk |
| 10,631,950 B2 | 4/2020 | Anderson |
| 10,962,197 B2 | 3/2021 | Vasylyev |
| 11,350,499 B2 | 5/2022 | Jung |
| 11,374,357 B2 | 6/2022 | Dobler |
| 11,381,043 B2 * | 7/2022 | Zhou .................. G02B 6/0083 |
| 2002/0018350 A1 | 2/2002 | Lepley |
| 2003/0006230 A1 | 1/2003 | Kaji |
| 2005/0210643 A1 | 9/2005 | Mezei |
| 2008/0030343 A1 | 2/2008 | Raybuck et al. |
| 2009/0171328 A1 | 7/2009 | Horvath |
| 2010/0027293 A1 | 2/2010 | Li |
| 2021/0307847 A1 * | 10/2021 | Laubenthal .......... A61B 90/361 |

OTHER PUBLICATIONS

Sunderland, Nicolas, "Shaping LED diffuser performance with polycarbonate materials", Covestro, 2017.

* cited by examiner

CONSOLE LIGHT GUIDE DEVICE

INTRODUCTION

The present disclosure relates to improved indicator lights for use with human-machine interface (HMI) devices having one or more output connection ports. Aspects of the present disclosure pertain to ophthalmic and other surgical consoles having a console panel on which such connection ports are purposefully arranged, typically in designated rows and columns. In such an arrangement, the connection ports are readily accessible by an attending surgeon through an exterior face of the console panel.

Console panels of typical surgical consoles are often constructed from a lightweight transparent material such as molded plastic or polycarbonate. For a given output connection port, an indicator light may be situated behind the console panel and selectively illuminated to indicate a corresponding port ON/OFF state, usage status, or another port status. However, existing indicator lights configured for this purpose tend to provide non-uniform brightness and color. Integration of indicator lights into the console can also exacerbate lighting non-uniformity when the console panel has a curved external face.

SUMMARY

Disclosed herein is a console light guide device for use with a control console having console panel. The console panel as contemplated herein includes an external face and an output connection port, with the external face possibly being outwardly curved or convex as summarized above. While the control console would ordinarily include multiple rows and columns of output connection ports, e.g., when embodied as an exemplary ophthalmic surgical console as set forth below, the terms "the output connection port" is used hereinafter for illustrative simplicity in the context of "at least one" or "one or more". In other words, the number and arrangement of such output connection ports may vary within the scope of the disclosure based on the particular application.

The console light guide device in accordance with an aspect of the disclosure includes an interconnected light tube array, multiple side-firing light-emitting diodes (LEDs), and an opaque light guard. The light tube array includes a translucent surface, a shaped body (e.g., an arcuate or other shaped body) at least partially surrounding the output connection port on the external face of the console panel, and a pair of linear branches arranged relative to the shaped body. The side-firing LEDs emit light laterally into a corresponding terminal end of the tube array such that the emitted light propagates along a longitudinal axis of constituent light tubes of the light tube array.

The opaque light guard may define a shaped channel and a pair of branch channels. The shaped body and the linear branches of the light tube array are configured to nest within the shaped channel and the branch channels. Light from the side-firing LEDs is thus emitted uniformly through the translucent surface with minimal internal scattering or bleeding within the control console.

Embodiments of the console light guide device include the shaped body and the linear branches forming single open-ended tubes, with the linear branches arranged tangentially to the shaped body. The corresponding end could optionally include four ends to incorporate four side-firing LEDs, without limiting the disclosure to such an embodiment.

The shaped body may be a C-shaped body defining a gap. In such an embodiment, the console light guide device may include a front-firing LED positioned radially outward from the gap and configured to backlight a graphic on the external face of the console panel. A baffle may be configured to focus light from the front-firing LED onto the graphic to thereby backlight the graphic. Respective longitudinal axes of the pair of linear branches may optionally intersect diametrically opposite the gap. In other embodiments, the shaped body may not include a gap (e.g., the shaped body may form a complete ring or other shape).

An aspect of the disclosure includes a respective one of the side-firing LEDs being individually driven by a printed circuit board assembly (PCBA). The interconnected light tube array and the opaque light guard in one or more embodiments includes axial mounting features and latches collectively configured to connect the console light guide device to a surface of the PCBA. The surface of the PCBA may be disposed opposite the translucent surface and coated with a reflective material in some implementations.

An aspect of the disclosure includes the interconnected light tube array being constructed of a transparent material. The translucent surface could be a roughened or textured section of the transparent material. A surface of the interconnected light tube array located opposite the translucent surface in such an embodiment may be coated with a reflective material.

The shaped body and the shaped channel could include two oppositely-positioned shaped bodies and two oppositely-positioned shaped channels. The linear branches and the linear channels in such an embodiment would connect corresponding ends of the two oppositely-positioned shaped bodies and the two oppositely-positioned shaped channels.

Also disclosed herein is a surgical console having a console housing and a console panel connectable thereto. The console panel, which has an external face and an internal face, is connected to the housing and includes an output connection port on the external face. The console light guide device is connected to the console panel.

The above-described features and advantages and other possible features and advantages of the present disclosure will be apparent from the following detailed description of the best modes for carrying out the disclosure when taken in connection with the accompanying drawings.

The solutions of the present disclosure may be modified or presented in alternative forms. Representative embodiments are shown by way of example in the drawings and described in detail below. However, inventive aspects of this disclosure are not limited to the disclosed embodiments. Rather, the present disclosure is intended to cover alternatives falling within the scope of the disclosure as defined by the appended claims.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure.

As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Figure 1:
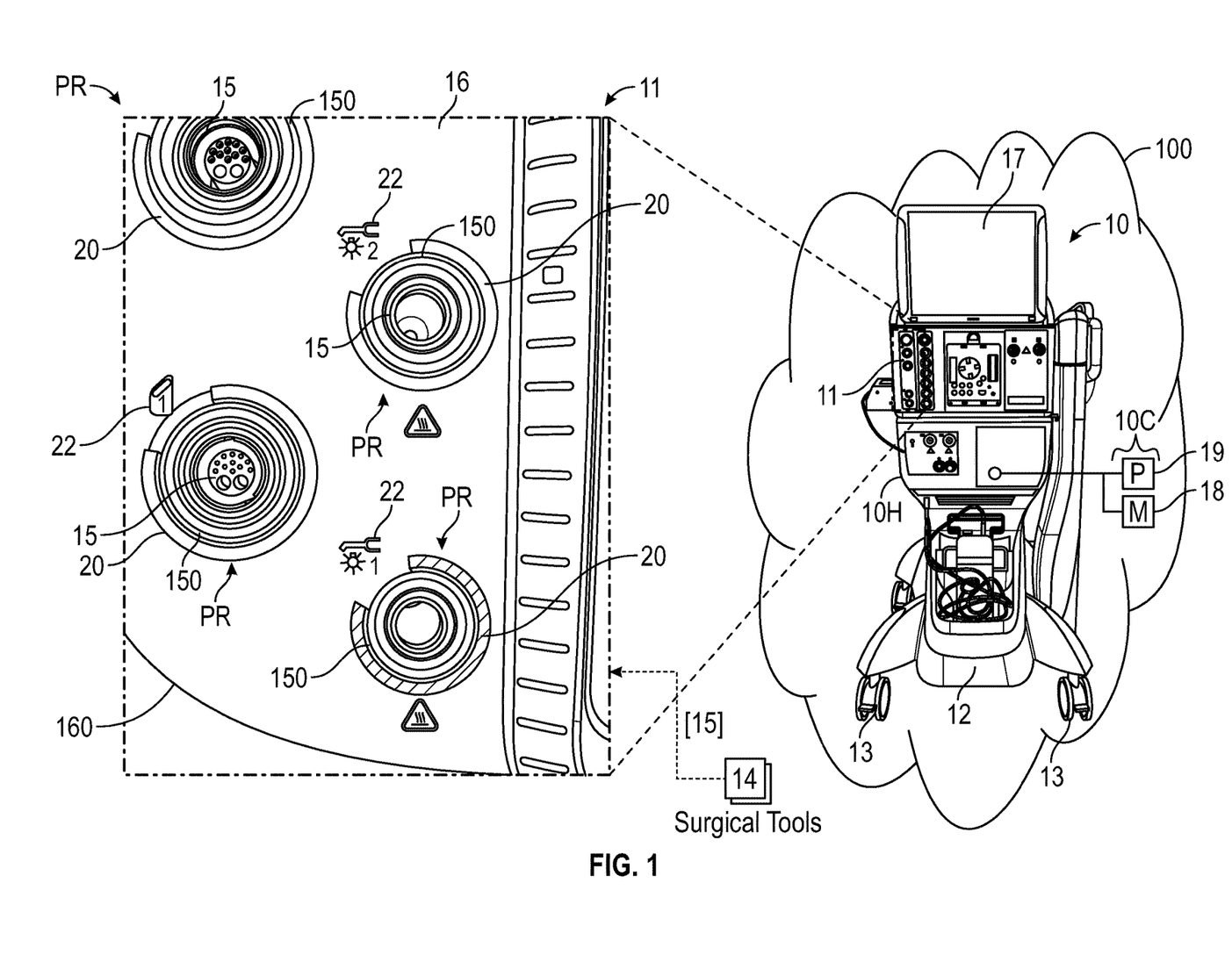
FIG. 1 illustrates a human-machine interface device in the form of a representative ophthalmic surgical console equipped with several output connection ports and a console light guide device configured as set forth herein.

Referring to the drawings, wherein like reference numbers refer to like components, a representative human-machine interface (HMI) device 100 is depicted in FIG. 1. The HMI device 100 in the depicted representative configuration includes a control console 10 having a console housing 10H. The particular size, shape, and internal/external configuration of the control console 10 may vary with the application, and therefore the control console 10 shown in FIG. 1 is representative of just one possible construction. The console housing 10H, e.g., a protective plastic or lightweight metal tower or box, contains electrical, pneumatic, data, hydraulic, or other application-specific conductors or conduit, control hardware, and associated software. With respect to the latter hardware and software elements, the control console 10 may include a local control system 10C having memory (M) 18 and a processor (P) 19 configured as set forth in further detail below.

The console housing 10H is additionally equipped with/connected to a console panel 11 having an external face 16. In one or more embodiments, the external face 16 may have an outwardly-curved or convex outer surface 160 through which is presented one or more output connection ports 15. The disclosed lighting solutions described in further detail below are directed towards improving both the structure and associated lighting control techniques used for selectively illuminating a corresponding outer periphery 150 of the various connection ports 15. In this manner, the control console 10 is configured to provide intuitive color-coded visual indication of a corresponding port status using, for example, a partial-ring (PR) appearance or an illuminated partial "halo". In other embodiments, other shapes may be used (e.g., a full ring, square, other custom shape, etc.)

The control console 10 of FIG. 1 may be securely mounted to a base 12, which in the illustrated non-limiting embodiment is connected to a set of casters 13. When the control console 10 is configured as an ophthalmic surgical console as shown, the surgical console 10 is maneuvered into a working position proximate an adjustable surgical chair or other platform on which a patient is situated. A variety of surgical tools 14, e.g., endo-illuminators, chandeliers, or other ophthalmic lighting devices, ultrasonic handpieces, proportional diathermy tools, vitrectors or other cutting tools, irrigation and/or suction tools, laser devices, etc., are then connected to corresponding output connection ports 15 through the external face 16 of the control console 10. The control console 10 may also include other functional components, such as a high-resolution display screen 17 suitable for viewing control and feedback information or other relevant data during the course of performing a procedure.

As briefly noted above, the exemplary control console 10 is operable, in the exemplary embodiment of FIG. 1, for controlling the operation of the various surgical tools 14. To that end, the control console 10 is programmed in software and equipped in hardware, i.e., "configured", to execute computer-readable instructions from its resident memory 18 using the processor 19. To that end, the memory 18 may include tangible non-transitory memory, e.g., optical, magnetic, flash, or other types of read only memory, along with application-sufficient amounts of random-access memory, electrically-erasable programmable read only memory, etc. The processor 19 may be constructed from various combinations of Application Specific Integrated Circuit(s) (ASICs), Field-Programmable Gate Arrays (FPGAs), electronic circuits, central processing units, microprocessors, and the like. Non-transitory components of the memory 18 store computer-readable instructions for controlling operation of the surgical tools 14 and the illumination functions described herein. The latter function of illumination control is achieved herein via specific placement and control of one or more console light guide devices 20.

The control console 10 depicted in FIG. 1 is equipped with one or more of the console light guide devices 20, which in turn are configured to provide a uniformly-lit shape (e.g., a partial ring, a full ring, or another shape) on the external face 16 of the console panel 11. In some embodiments, each shape may substantially circumscribe the outer periphery 150 of a corresponding one of the connection ports. As used herein, "substantially circumscribes" for the circular shape of the outer periphery 150 means "surrounding close to but less than a full 360° circumference of", e.g., about 300° to about 320° depending on the embodiment. Other shapes are also contemplated. For example, a full ring that circumscribes the port, a square, an oval, a custom shape, etc. Features of the console light guide device 20 as described herein collectively enable integration of the console light guides with the external face 16.

As noted above, the external face 16 may be outwardly curved or convex to form the curved surface 160. In such a construction, lighting discrepancies could be more noticeable to users of the control console 10. This is largely due to different distances of separation between the external face 16 and internal lighting sources, shown in FIG. 3 as side-firing light-emitting diodes (LEDs) 40. A solution to this particular problem lies in the projection of light laterally into structure of the console light guide device 20, i.e., using a "side-fired" arrangement, rather than directly outward through the external face 16 in the manner of a typical backlit device.

Each console light guide of FIG. 1 may be selectively illuminated by the electronic control unit 10C in an application-specific manner. For example, a given one of the console light guides could be illuminated in a color-coded manner, such as using green, blue, or amber. The displayed colors are used to notify a surgeon or another user of the control console 10 as to the current port status of the corresponding output connection port 15 that, for example, may be substantially circumscribed by the console light guide (which may be a partial-ring (PR) or other shape). The term "port status" as used herein may entail an ON/OFF status of the connection port 15, or a level of "fading" to indicate different meanings such as "needs attention" or additional steps to render the connection port 15 ready for use, or a selected function or connection status, a fault status, an activation status, etc. As appreciated in the art, meanings are assigned to each possible color or color combination so that users of the control console 10 are made aware at a glance of the current port status, thus allowing the user to focus on the tasks at hand.

Additionally, the external face 16 of the console panel 11 shown in FIG. 1 may include, either as part of the console light guide device 20 or separately, artwork in the form of an icon, symbol, or other graphic 22 adjacent each respective one of the output connection ports 15. The graphic 22, which in just one possible implementation could be laser etched into the material of the console panel 11, could be used to identify the particular function of the output connection port 15. The console panel 11 in one or more embodiments could be constructed as an in-mold decoration (IMD) part, which as appreciated in the art could have a plastic wall molded behind a plastic film, both omitted for simplicity. The plastic film could be constructed of several ink print layers, including a white diffusion print layer to help further diffuse the light. The plastic wall's translucency would also act as a diffuser. As part of the present solution, such graphics 22 could be back-lit using the illumination of the console light guide. In some embodiments, graphics 22 could form an integral part of the console light guide device 20 as set forth below, either together or apart from the illumination of the console light guides, with minimal (ideally none of) light being scattered or leaked within the control console 10.

Figure 2:
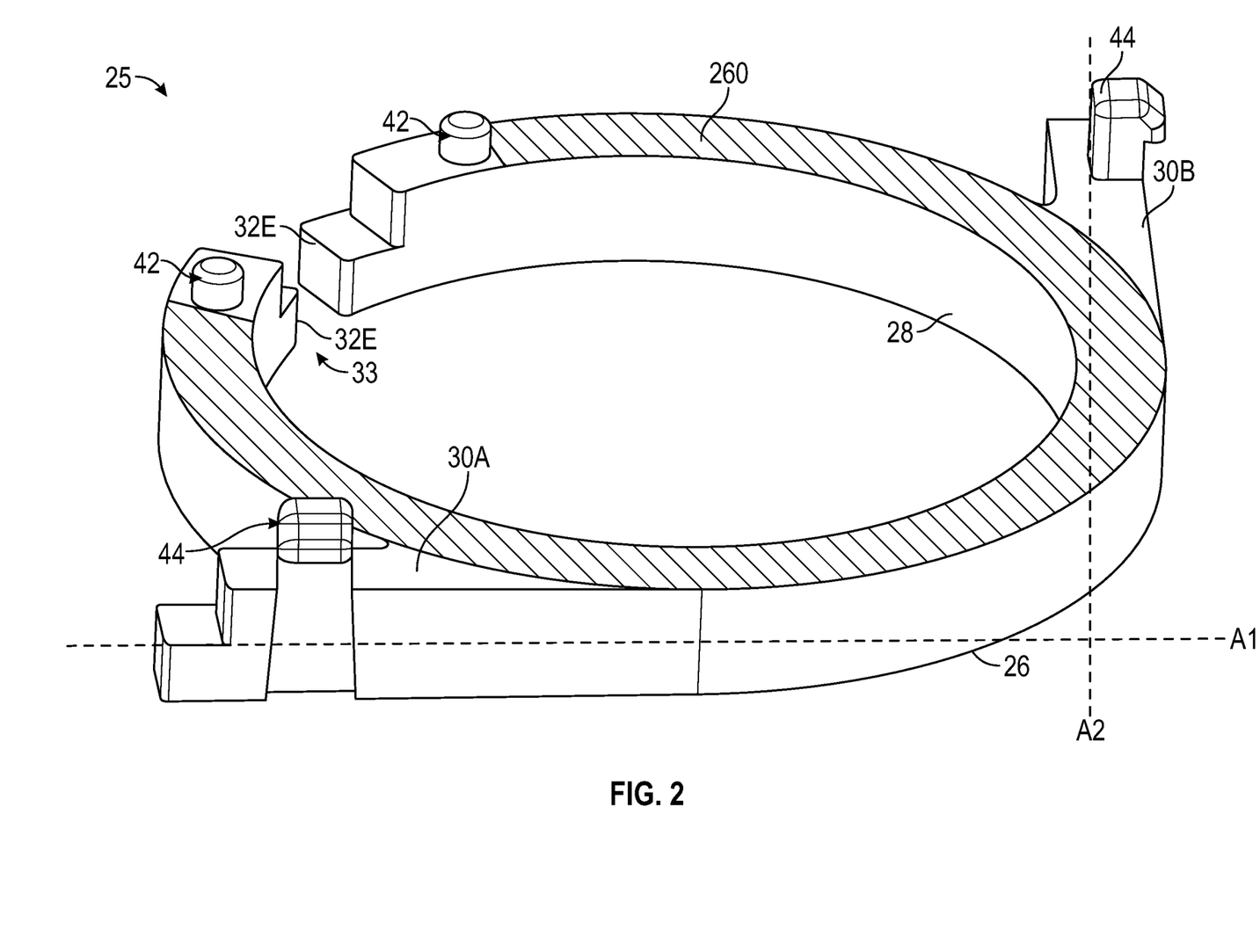
FIG. 2 is a perspective view illustration of a light guide tube array usable as part of the console light guide device shown in FIG. 1.

Referring now to FIG. 2, the console light guide device 20 of FIG. 1 as contemplated herein includes an interconnected light tube array 25 forming a light-guiding conduit network within the scope of the present disclosure. The light tube array 25 in the illustrated embodiment includes a ring-shaped or other shaped body 28 having a translucent outer surface 26 and a reflective inner surface 260. FIG. 2 depicts the light tube array 25 in an "upside-down" orientation, and thus "outer" and "inner" in this orientation refer to the relative position of the surfaces 26 and 260 with respect to a user of the control console 10 of FIG. 1. In other words, the translucent outer surface 26 is the visible surface of the console light guide device 20 when used to form the above-noted illuminated console light guide. The translucent outer surface 26 in one or more embodiments may be a roughened or textured section of an otherwise transparent material, e.g., polycarbonate, nylon, plastic, acrylic, etc. The reflective inner surface 260 for its part, located opposite the translucent outer surface, may be a pad-printed layer of a white, silver, polished mirror, or another reflective material suitable for reflecting incident light back through the translucent outer surface 26.

The light tube array 25 of FIG. 2 also includes a pair of linear branches 30A, 30B each arranged relative to and intersecting the shaped body 28. The shaped body 28 and the linear branches 30A, 30B thus collectively form or define constituent light-guiding sections of the interconnected light tube array 25. In this particular embodiment, the shaped body 28 and the linear branches 30A, 30B are configured as single open-ended tubes, with respective longitudinal center axes A1, A2 of the branches 30A, 30B arranged tangentially to the shaped body 28. However, other arrangements may be contemplated within the scope of the present disclosure.

As illustrated in FIG. 2, in some embodiments, the shaped body 28 may form less than a full 360° ring or circle. Instead, the shaped body 28 may be considered to be generally C-shaped. That is, a small annular gap 33 may be present between opposing ends 32E of the shaped body 28. The annular gap 33 in turn may be positioned adjacent to a respective one of the above-noted graphics 22 of FIG. 1, with back-illumination of the graphic 22 thus used to illuminate and accentuate the graphic 22. In some embodiments, the shaped body 28 may form a full 360° ring or circle or may form a different partial or complete shape. As part of the present approach, the light tube array 25 also includes mounting features 42 disposed on the inner surface 260 of the shaped body 28. The light tube array 25 also includes latches 44 disposed on the linear branches 30A, 30B. The mounting features 42 and latches 44, along with other structural elements as described below, together serve to connect the light tube array 25 to the PCBA 35 of FIG. 3.

Figure 3:
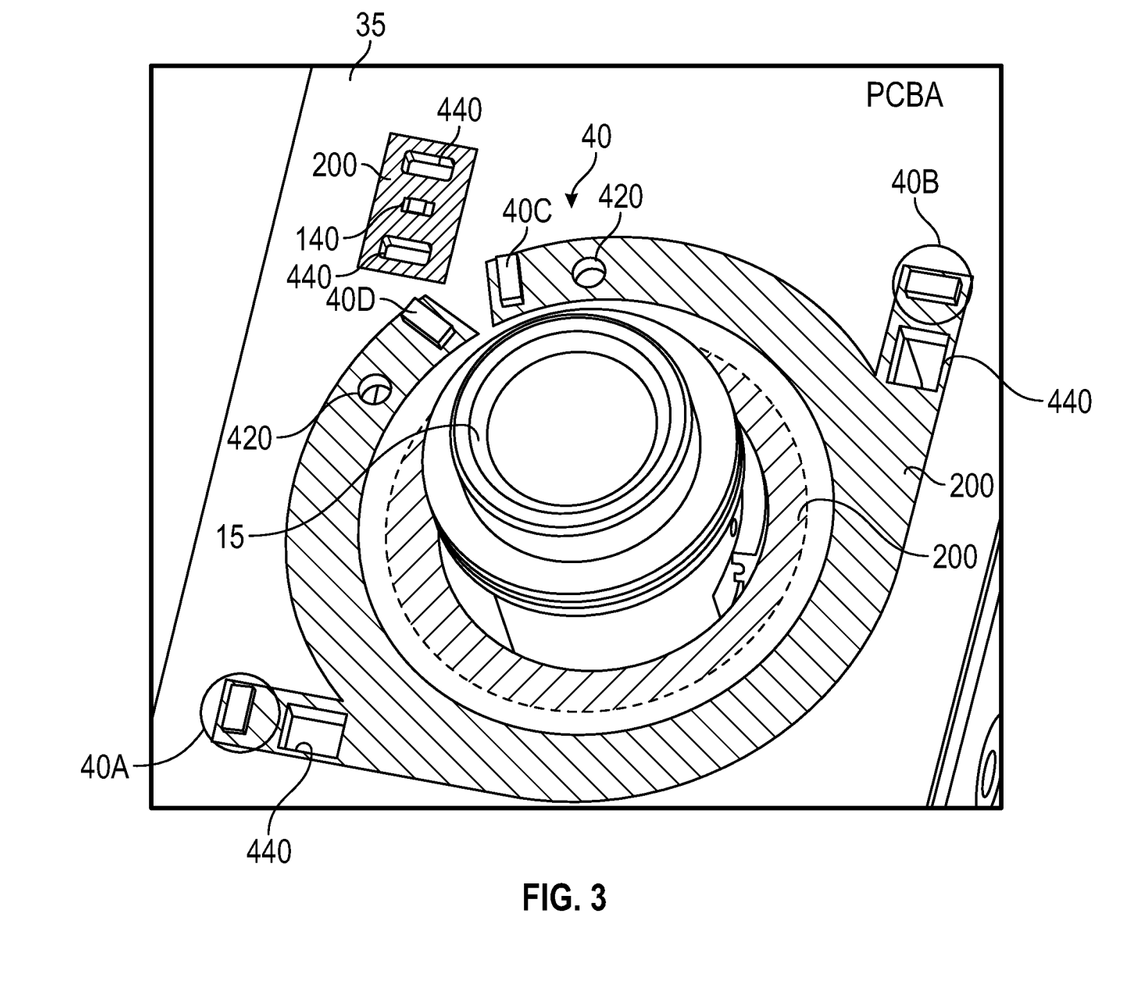
FIG. 3 illustrates a representative placement, spacing, and side-emitted light trajectories for side-firing light-emitting diodes (LEDs) of the console light guide device in accordance with an aspect of the disclosure.

LIGHTING CONTROL: Referring briefly to FIG. 3, the console light guide device 20 of FIG. 1 also includes or is mounted to the above-noted PCBA 35. The PCBA 35, which may also include the memory 18 and the processor 19 as shown in FIG. 1, can be controlled using computer-readable and executable instructions recorded in associated portions of the memory 18. A designated "keep out" area 200 of the console light guide device 20 is indicated to illustrate areas for a designer of the PCBA 35 to avoid placing electrical components unrelated to the console light guide device 20.

In accordance with an aspect of the disclosure, the side-firing LEDs 40 are purposefully arranged on the PCBA 35 at the indicated relative positions and configured to laterally transmit light into the interconnected light tube array 25 shown in FIG. 2. In a non-limiting implementation of the present teachings, the side-firing LEDs 40 may include four representative side-firing LEDs 40A, 40B, 40C, and 40D. This particular representative number and arrangement may provide an optimal tradeoff between ideal lighting qualities and number of side-firing LEDs 40 in one or more use cases. For instance, two of the side-firing LEDs 40, such as LEDs 40A and 40B proximate the ends 32E of FIG. 2, could be used to boost brightness in a middle segment of the console light guide of FIG. 1. However, more or fewer side-firing LEDs 40 could be used in other implementations without departing from the intended scope of the disclosure.

Additionally, each console light guide device 20 contemplated herein may include a front-firing LED 140 set a short distance apart from the side-firing LEDs 40. In a possible implementation, the front-firing LED 140 could be embodied as white LED or an LED that illuminates in another application-suitable color. The front-firing LED 140 is positioned radially outward from the annular gap 33 shown in FIG. 2. This location places the front-firing LED 140 directly behind the graphic 22 of FIG. 1 relative to a user of the control console 10, and thus provides back-illumination or back-lighting of the graphic 22 as noted above.

In the exemplary construction of FIG. 3, each respective one of the side-firing LEDs 40 and the front-firing LED 140 is individually-addressable by operation of the PCBA 35. As appreciated in the art, individually-addressable or so-called "smart" LEDs have a unique assigned address, and thus can be independently controlled and illuminated by corresponding electronic signals from the processor 19, as opposed to having to illuminate all of the LEDs 40, 140 or groups thereof in unison. To this end, each of the LEDs 40 and 140 may be surface-mounted to the PCBA 35. The PCBA 35 in turn is connected to or driven by the processor 19 via an appropriate protocol and transfer conductors to control brightness, color, timing, and other desirable properties. In a likely embodiment, the front-firing LED 140 would remain lit while the control console 10 of FIG. 1 is in operation, or at least for the duration that the corresponding output connection port 15 is in use.

As output connection port 15 may be used at different times during a given procedure, the corresponding illuminated color of the console light guide of FIG. 1 will likewise change in response to changes in the port status. To enable a fast-responding dynamic color change, the side-firing LEDs 40 of FIG. 3 could be implemented as multi-channel red-green-blue (RGB) LED arrays, possibly with a controller chip integrated into a single circuit board package. Thus, the processor 19 and the associated circuitry of the PCBA 35 are able to adapt to failures of individual side-firing LEDs 40 to maintain the desired lighting uniformity as set forth herein. That is, rather than a user experiencing dark spots in the illuminated console light guide of FIG. 1, which could occur using conventional backlighting and equally-spaced back-firing LEDs, the loss or performance degradation of a single LED 40 could be compensated for using the present approach simply by adjusting control settings of the remaining/functioning side-firing LEDs 40.

Figure 4:
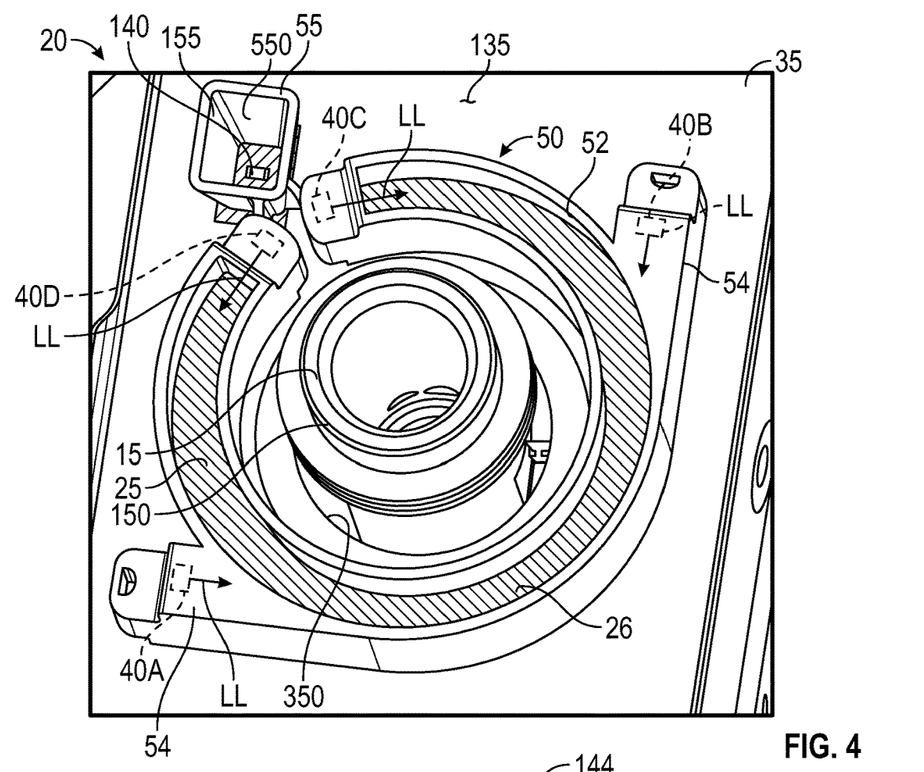
FIGS. 4 and 5 are respective top and bottom views of an opaque light guard usable as part of the console light guide device of the present disclosure.
Figure 5:
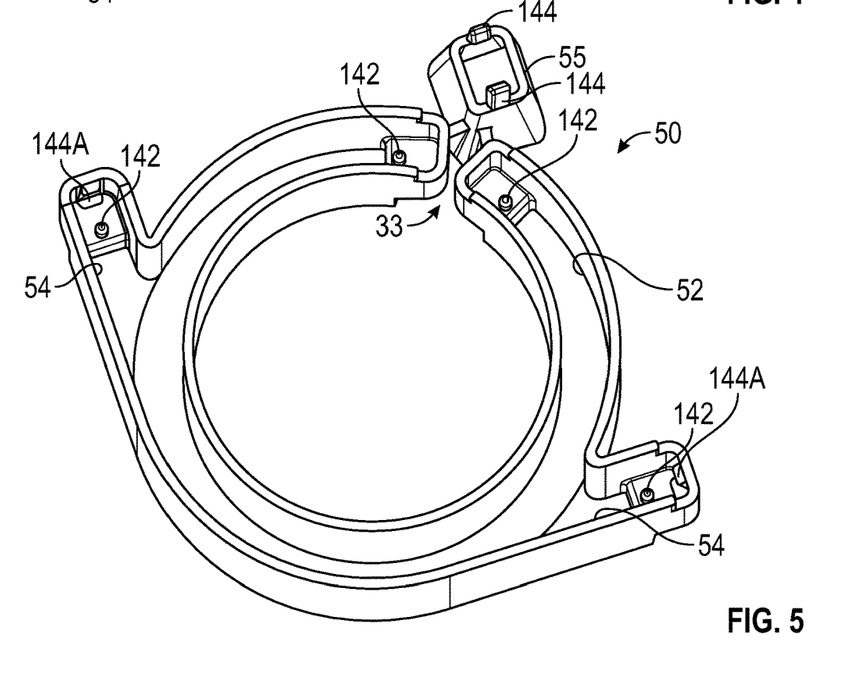

Referring now to FIGS. 4 and 5, each console light guide device 20 further includes an opaque light guard 50. The opaque light guard 50 works in concert with the interconnected light tube array 25, shown engaged with the opaque light guard 50 in FIG. 4, to direct light emitted by the respective side-firing and front-firing LEDs 40 and 140 through the translucent outer surface 26 of the shaped body 28. The opaque light guard 50 does this while also preventing undesirable light bleed within the control console 10 of FIG. 1, between adjacent console light guides, and between illuminated graphics 22. As noted below, the use of white or other reflective colors on portions of the opaque light guard 50 could help increase overall brightness output of the collective LEDs 40 and 140.

In the illustrated exemplary configuration of FIG. 4, the opaque light guard 50 surrounds an opening 350 in the PCBA 35 through which the output connecting port 15 protrudes. For additional light bleed prevention, the opaque light guard 50 further includes a baffle 55 defining a cavity 155 therewithin, with the front-firing LED 140 being disposed within the cavity 155 and surrounded on all sides by baffle walls 550. The baffle 55 thus projects outward from an external surface 135 of the PCBA 35. The opaque light guard 50 and the baffle 55 are therefore configured and arranged to minimize undesirable light bleed between adjacent console light guides on the control console 10 of FIG. 1, as well as to minimize any light bleed between the illuminated graphics 22 and other structure of the control console 10.

The opaque light guard 50 of FIGS. 4 and 5 also defines a shaped channel 52 and a pair of linear branch channels 54. Counterpart structure of the interconnected light tube array 25 shown in FIG. 2, i.e., the shaped body 28 and the linear branches 30A, 30B (see FIG. 2), is configured to securely nest within the shaped channel 52 and the pair of linear branch channels 54, respectively, as best shown in FIG. 4. Once engaged in this manner, light (arrows LL) from the side-firing LEDs 40 of FIG. 3, e.g., LEDs 40A, 40B, 40C, and 40C, is emitted uniformly through the translucent outer surface 26 of the interconnected light tube array 25, and ultimately through the external face 16 of the console panel 11 depicted in FIG. 1, thereby forming the console light guides.

PCBA ENGAGEMENT FEATURES: As shown in FIGS. 3-5, the console light guide device 20 is also equipped herein with multiple different engagement features collectively suitable for attaching the console light guide device 20 to the PCBA 35 of FIG. 3. For instance as shown in FIG. 2, the light tube array 25 could include one or more of the axial mounting features 42, e.g., cylindrical alignment pins or posts, and one or more of the latches 44, for instance locking tabs or snap hooks. Similarly, the opaque light guard 50 of FIG. 5 could be equipped with similar axial mounting features 142 and latches 144, 144A. Thus, installation of the console light guide device 20 to the PCBA 35 could entail pressing the axial mounting features 42, 142 and the latches 44, 144 into mating slots or openings 420, 440 in the PCBA 35 (see FIG. 3) in a "push-to-connect" manner. The latches 144A could then mate with accompanying slot structure of the light tube array 25. A thin nominal wall thickness of the axial mounting features 42, 142 and the latches 44, 144 would help render such components sufficiently deflectable and resilient for this purpose.

Figure 6:
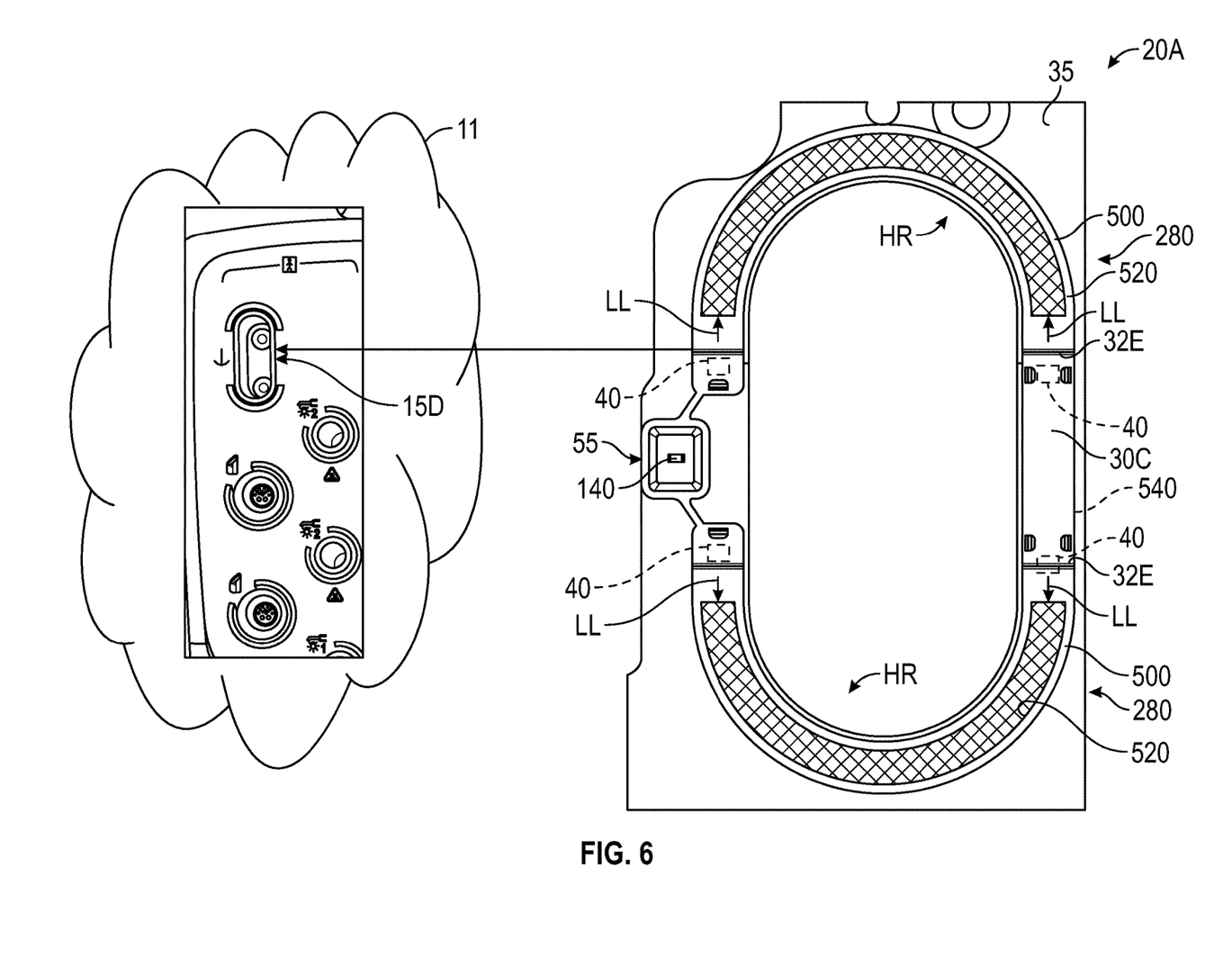
FIG. 6 illustrates a construction of the console light guide device for use with an alternatively-configured dual connection port.

An alternative console light guide device 20A is illustrated in FIG. 6. As appreciated in the art, some of the above-described output connection ports 15 arranged on the console panel 11 of FIG. 1 could be configured as dual connection ports 15D, e.g., a proportional diathermy port. The shaped body 28 and the shaped channel 52 described above in this case could be adapted to fit the dual connection port 15D, e.g., using two oppositely-positioned shaped bodies 280 and two oppositely-positioned shaped channels 520, with the shaped bodies 280 forming "half-ring" segments (HR). A modified opaque light guard 500, e.g., a semicircular shape, could be used to perform the functions of the above-described opaque light guard 50.

In this embodiment, one or more linear branches 30C and linear channels 540 situated therewithin could connect the ends 32E of the two oppositely-positioned shaped bodies 280 and the two oppositely-positioned shaped channels 520. Each half-ring segment (HR) of the alternative console light guide device 20A of FIG. 6 may then be illuminated by two side-firing LEDs 40 in a possible construction. Implementation of the console light guide device 20A of FIG. 6 would otherwise be as described above.

The foregoing disclosure thus improves upon the state of the art of typical light rings. A particular problem associated with the current state of the art is the relative difficulty of achieving shaped illumination with a uniform brightness and color utilizing a minimal number of LEDs. Typical approaches use as many as twelve or more front-firing LEDs similar to the single front-firing LED 140 of FIGS. 3 and 4, and perhaps a front diffuser panel to achieve some semblance of uniformity. A dark spot could result in the illumination shape in the event one or more of the LEDs fails. The individually-addressable LEDs 40 and the curvilinear configuration of the console light guide device 20 described above thus solves these and other potential challenges associated with achieving uniform brightness and color, optimal bending of light, and optimal projection of the bent light through a plastic panel having a curved surface, e.g., the external surface 16 of the console panel 11 shown in FIG. 1. These and other attendant benefits of the present disclosure will be readily appreciated by those skilled in the art now having the advantage of the present disclosure.

Embodiments shown in the drawings or the characteristics of various embodiments mentioned in the present description are not necessarily to be understood as embodiments independent of each other. It is possible each of the characteristics described in one of the examples of an embodiment can be combined with one or a plurality of other desired characteristics from other embodiments, resulting in other embodiments not described in words or by reference to the drawings.

Accordingly, such other embodiments fall within the framework of the scope of the appended claims. The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

The invention claimed is:

1. A console light guide device for use with a control console having a console panel and an output connection port, comprising:
　an interconnected light tube array having a translucent surface, a shaped body configured to at least partially surround the output connection port on an external face of the console panel, and at least one linear branch arranged relative to the shaped body;
　a plurality of side-firing light-emitting diodes (LEDs), wherein each respective one of the side-firing LEDs is configured to emit light into a corresponding end of the interconnected light tube array; and
　an opaque light guard defining a shaped channel and at least one corresponding branch channel, wherein the interconnected light tube array is configured to nest within the shaped channel and the at least one branch channel of the opaque light guard, such that the light from the side-firing LEDs is emitted uniformly through the translucent surface without internal scattering or bleeding of the light within the control console;
　wherein the shaped body and the at least one linear branch are configured as single open-ended tubes, and wherein the at least one linear branch is arranged tangentially to the body.

2. The console light guide device of claim 1, wherein the corresponding end includes four ends, and wherein the plurality of side-firing LEDs equals four side-firing LEDs.

3. A console light guide device for use with a control console having a console panel and an output connection port, comprising:
　an interconnected light tube array having a translucent surface, a shaped body configured to at least partially surround the output connection port on an external face of the console panel, and at least one linear branch arranged relative to the shaped body;
　a plurality of side-firing light-emitting diodes (LEDs), wherein each respective one of the side-firing LEDs is configured to emit light into a corresponding end of the interconnected light tube array; and
　an opaque light guard defining a shaped channel and at least one corresponding branch channel, wherein the interconnected light tube array is configured to nest within the shaped channel and the at least one branch channel of the opaque light guard, such that the light from the side-firing LEDs is emitted uniformly through the translucent surface without internal scattering or bleeding of the light within the control console;
　wherein the shaped body includes a C-shaped body defining a gap, the console light guide device further comprising:
　a front-firing LED positioned radially outward from the gap and configured to backlight a graphic on the external face of the console panel; and
　a baffle configured to focus light from the front-firing LED onto the graphic to thereby backlight the graphic.

4. The console light guide device of claim 3, wherein the at least one linear branch comprises a pair of linear branches and wherein respective longitudinal axes of the pair of linear branches intersect diametrically opposite the gap.

5. The console light guide device of claim 1, wherein each respective one of the side-firing LEDs is individually driven via a printed circuit board assembly (PCBA), and wherein the interconnected light tube array and the opaque light guard include one or more axial mounting features and latches collectively configured to connect the console light guide device to a surface of the PCBA.

6. The console light guide device of claim 5, wherein the surface of the PCBA is disposed opposite the translucent surface and coated with a reflective material.

7. The console light guide device of claim 1, wherein the interconnected light tube array is constructed of a transparent material, the translucent surface is a roughened or textured section of the transparent material, and a surface of the interconnected light tube array located opposite the translucent surface is coated with a reflective material.

8. A console light guide device for use with a control console having a console panel and an output connection port, comprising:
　an interconnected light tube array having a translucent surface, a shaped body configured to at least partially surround the output connection port on an external face of the console panel, and at least one linear branch arranged relative to the shaped body;
　a plurality of side-firing light-emitting diodes (LEDs), wherein each respective one of the side-firing LEDs is configured to emit light into a corresponding end of the interconnected light tube array; and
　an opaque light guard defining a shaped channel and at least one corresponding branch channel, wherein the interconnected light tube array is configured to nest within the shaped channel and the at least one branch channel of the opaque light guard, such that the light from the side-firing LEDs is emitted uniformly through the translucent surface without internal scattering or bleeding of the light within the control console;
　wherein the shaped body and the shaped channel include two oppositely-positioned shaped bodies and two oppositely-positioned shaped channels, and wherein the at least one linear branch and the at least one linear channel connect corresponding ends of the two oppositely-positioned shaped bodies and the two oppositely-positioned shaped channels.

9. A control console, comprising:
　a console housing;

a console panel having an external face and an internal face, wherein the console panel is connected to the housing and includes an output connection port on the external face; and
a console light guide device connected to the console panel, including:
an interconnected light tube array having a translucent surface;
an arcuate-shaped body configured to at least partially surround the output connection port on an external face of the console panel;
a pair of linear branches arranged relative to the arcuate-shaped body;
a plurality of side-firing light-emitting diodes (LEDs), wherein each respective one of the side-firing LEDs is configured to emit light into a corresponding end of the interconnected light tube array; and
an opaque light guard defining an arcuate-shaped channel and a pair of branch channels, wherein the interconnected light tube array is configured to nest within the arcuate-shaped channel and the pair of branch channels of the opaque light guard, such that the light from the side-firing LEDs is emitted uniformly through the translucent surface without internal scattering or bleeding of the light within the control console;
wherein the arcuate-shaped body includes a C-shaped body defining an arcuate gap, the console light guide device further comprising:
a front-firing LED positioned radially outward from the arcuate-shaped gap and configured to backlight a graphic on the external face of the console panel; and
a baffle configured to focus light from the front-firing LED onto the graphic to thereby backlight the graphic.

10. The control console of claim 9, wherein each respective one of the side-firing LEDs is individually driven via a printed circuit board assembly (PCBA), and wherein the interconnected light tube array and the opaque light guard include one or more axial mounting features and latches collectively configured to connect the console light guide device to a surface of the PCBA.

11. The control console of claim 9, wherein the interconnected light tube array is constructed of a transparent material, and wherein the translucent surface is a roughened or textured section of the transparent material.

12. A control console, comprising:
a console housing;
a console panel having an external face and an internal face, wherein the console panel is connected to the housing and includes an output connection port on the external face; and
a console light guide device connected to the console panel, including:
an interconnected light tube array having a translucent surface;
an arcuate-shaped body configured to at least partially surround the output connection port on an external face of the console panel;
a pair of linear branches arranged relative to the arcuate-shaped body;
a plurality of side-firing light-emitting diodes (LEDs), wherein each respective one of the side-firing LEDs is configured to emit light into a corresponding end of the interconnected light tube array; and
an opaque light guard defining an arcuate-shaped channel and a pair of branch channels, wherein the interconnected light tube array is configured to nest within the arcuate-shaped channel and the pair of branch channels of the opaque light guard, such that the light from the side-firing LEDs is emitted uniformly through the translucent surface without internal scattering or bleeding of the light within the control console;
wherein the arcuate-shaped body and the arcuate-shaped channel include two oppositely-positioned arcuate-shaped bodies and two oppositely-positioned arcuate-shaped channels, and wherein the linear branches and the linear channels connect corresponding ends of the two oppositely-positioned arcuate-shaped bodies and the two oppositely-positioned arcuate-shaped channels.

13. The control console of claim 9, wherein the control console is configured as an ophthalmic surgical console, the external face is outwardly curved or convex, and the output connection port includes a plurality of connection ports each configured to connect to a corresponding ophthalmic surgical tool.

14. The console light guide device of claim 3, wherein each respective one of the side-firing LEDs is individually driven via a printed circuit board assembly (PCBA), and wherein the interconnected light tube array and the opaque light guard include one or more axial mounting features and latches collectively configured to connect the console light guide device to a surface of the PCBA.

15. The console light guide device of claim 14, wherein the surface of the PCBA is disposed opposite the translucent surface and coated with a reflective material.

16. The console light guide device of claim 3, wherein the interconnected light tube array is constructed of a transparent material, the translucent surface is a roughened or textured section of the transparent material, and a surface of the interconnected light tube array located opposite the translucent surface is coated with a reflective material.

17. The console light guide device of claim 8, wherein each respective one of the side-firing LEDs is individually driven via a printed circuit board assembly (PCBA), and wherein the interconnected light tube array and the opaque light guard include one or more axial mounting features and latches collectively configured to connect the console light guide device to a surface of the PCBA.

18. The console light guide device of claim 17, wherein the surface of the PCBA is disposed opposite the translucent surface and coated with a reflective material.

19. The console light guide device of claim 8, wherein the interconnected light tube array is constructed of a transparent material, the translucent surface is a roughened or textured section of the transparent material, and a surface of the interconnected light tube array located opposite the translucent surface is coated with a reflective material.

* * * * *